(12) United States Patent
Similowski et al.

(10) Patent No.: US 9,761,112 B2
(45) Date of Patent: Sep. 12, 2017

(54) ASSISTANCE TERMINAL FOR REMOTELY MONITORING A PERSON CONNECTED TO A MEDICAL ASSISTANCE AND MONITORING DEVICE

(75) Inventors: Thomas Similowski, Issy-les-Moulineaux (FR); Jesus Gonzalez-Bermejo, Montlignon (FR); Christian Straus, Guyancourt (FR); Julien Hurbault, Boulogne (FR); Didier Foret, Paris (FR); Nathalie Franckhauser, Maisons Alfort (FR); Sylvie Rouault, Chatenay-Malabry (FR)

(73) Assignee: UNIVERSITE PIERRE ET MARIE CURIE (PARIS 6), Paris (FR)

( * ) Notice: Subject to any disclaimer, the term of this patent is extended or adjusted under 35 U.S.C. 154(b) by 610 days.

(21) Appl. No.: 13/983,640

(22) PCT Filed: Feb. 14, 2012

(86) PCT No.: PCT/EP2012/052501
§ 371 (c)(1),
(2), (4) Date: Sep. 23, 2013

(87) PCT Pub. No.: WO2012/110504
PCT Pub. Date: Aug. 23, 2012

(65) Prior Publication Data
US 2013/0328685 A1    Dec. 12, 2013

(30) Foreign Application Priority Data
Feb. 14, 2011 (FR) ..................... 11 51192

(51) Int. Cl.
G08B 21/00 (2006.01)
G08B 21/18 (2006.01)
(Continued)

(52) U.S. Cl.
CPC ............ *G08B 21/187* (2013.01); *A61B 5/002* (2013.01); *A61B 5/0004* (2013.01);
(Continued)

(58) Field of Classification Search
CPC ............... A61B 5/0013; G08B 21/187; A61M 2205/3561
(Continued)

(56) References Cited

U.S. PATENT DOCUMENTS 4,827,935 A * 5/1989 Geddes ................ A61N 1/3601
                                                        600/536
5,228,449 A * 7/1993 Christ ................ A61B 5/02433
                                                        379/38
(Continued)

FOREIGN PATENT DOCUMENTS

JP    2006-271821 A    10/2006
WO   2009/153535 A2   12/2009

OTHER PUBLICATIONS

Machine Translation of FR2009051193, Medical Warning System and Method, printed Oct. 15, 2015, 9 pages.*

*Primary Examiner* — John A. Tweel, Jr.
*Assistant Examiner* — Adnan Aziz
(74) *Attorney, Agent, or Firm* — Sughrue Mion, PLLC

(57) ABSTRACT

The invention relates to an assistance terminal (5, 6a, 6b) including a housing (5) and at least one terminal (6a, 6b) for remotely monitoring a person (1) connected to a medical assistance and/or monitoring device (3). According to the invention, the housing (5) comprises:
  reception means (8) for receiving a signal from the medical device (3);
  conditioning means (9) for conditioning the signal received by the reception means (8) of the housing (5);
  storage means (10) for, in a learning phase prior to a phase of use of the terminal (5, 6a, 6b), storing a range of
(Continued)

signals which are sent by the medical device (3), and which are received by the reception means (8) of the housing (5) and which are conditioned by the conditioning means (9);

comparison means (11) for, during the phase of use of the terminal (5, 6a, 6b), comparing a signal sent by the medical device (3), received by the reception means (8) and conditioned by the conditioning means (9), with the signals previously stored;

transmission means (12) for, during the phase of use, transmitting the signal, if the latter corresponds to a signal previously stored, to the remote terminal (6a, 6b); the terminal (6a, 6b) comprising means for playing back the signal to at least one person to notify him or her of the sending of said signal by the device.

20 Claims, 2 Drawing Sheets

(51) Int. Cl.
*A61B 5/00* (2006.01)
*A61M 16/00* (2006.01)
*A61G 7/05* (2006.01)
*A61G 12/00* (2006.01)

(52) U.S. Cl.
CPC .......... *A61B 5/0013* (2013.01); *A61B 5/6824* (2013.01); *A61G 7/0515* (2016.11); *A61M 16/0051* (2013.01); *A61B 5/486* (2013.01); *A61B 2505/00* (2013.01); *A61G 12/002* (2013.01); *A61G 2210/30* (2013.01); *A61M 2205/18* (2013.01); *A61M 2205/3375* (2013.01); *A61M 2205/3553* (2013.01); *A61M 2205/3561* (2013.01); *A61M 2205/3584* (2013.01); *A61M 2205/3592* (2013.01); *A61M 2205/52* (2013.01)

(58) Field of Classification Search
USPC ...... 340/573.1, 539.11, 539.12, 539.17, 679; 348/143
See application file for complete search history.

(56) References Cited

U.S. PATENT DOCUMENTS

| | | | |
|---|---|---|---|
| 5,651,070 A | 7/1997 | Blunt | |
| 5,971,921 A * | 10/1999 | Timbel | G08B 25/016 128/904 |
| 6,160,478 A * | 12/2000 | Jacobsen | A61B 5/0022 128/903 |
| 6,360,740 B1 * | 3/2002 | Ward | A61N 1/3601 128/200.24 |
| 6,415,183 B1 * | 7/2002 | Scheiner | A61N 1/3601 607/42 |
| 6,463,327 B1 * | 10/2002 | Lurie | A61H 31/00 607/42 |
| 7,363,086 B1 * | 4/2008 | Koh | A61N 1/3601 607/118 |
| 8,244,359 B2 * | 8/2012 | Gelfand | A61N 1/3601 607/116 |
| 8,355,792 B2 * | 1/2013 | Alataris | A61N 1/36071 607/117 |
| 8,764,651 B2 * | 7/2014 | Tran | A61B 5/4076 600/300 |
| 2003/0195571 A1 * | 10/2003 | Burnes | A61N 1/3601 607/9 |
| 2004/0155770 A1 | 8/2004 | Nelson et al. | |
| 2005/0080461 A1 * | 4/2005 | Stahmann | A61B 5/0031 607/17 |
| 2005/0197588 A1 * | 9/2005 | Freeberg | A61B 5/0031 600/529 |
| 2006/0017558 A1 | 1/2006 | Albert et al. | |
| 2006/0142815 A1 * | 6/2006 | Tehrani | A61N 1/3601 607/42 |
| 2006/0189863 A1 * | 8/2006 | Peyser | A61B 5/0031 600/345 |
| 2006/0247729 A1 * | 11/2006 | Tehrani | A61N 1/3601 607/42 |
| 2008/0018435 A1 * | 1/2008 | Brown | G06F 19/3418 340/286.07 |
| 2009/0189771 A1 * | 7/2009 | Liu | G08B 21/0476 340/573.1 |
| 2011/0004072 A1 * | 1/2011 | Fletcher | A61B 5/0002 600/300 |
| 2011/0184488 A1 * | 7/2011 | De Ridder | A61N 1/36071 607/46 |

* cited by examiner

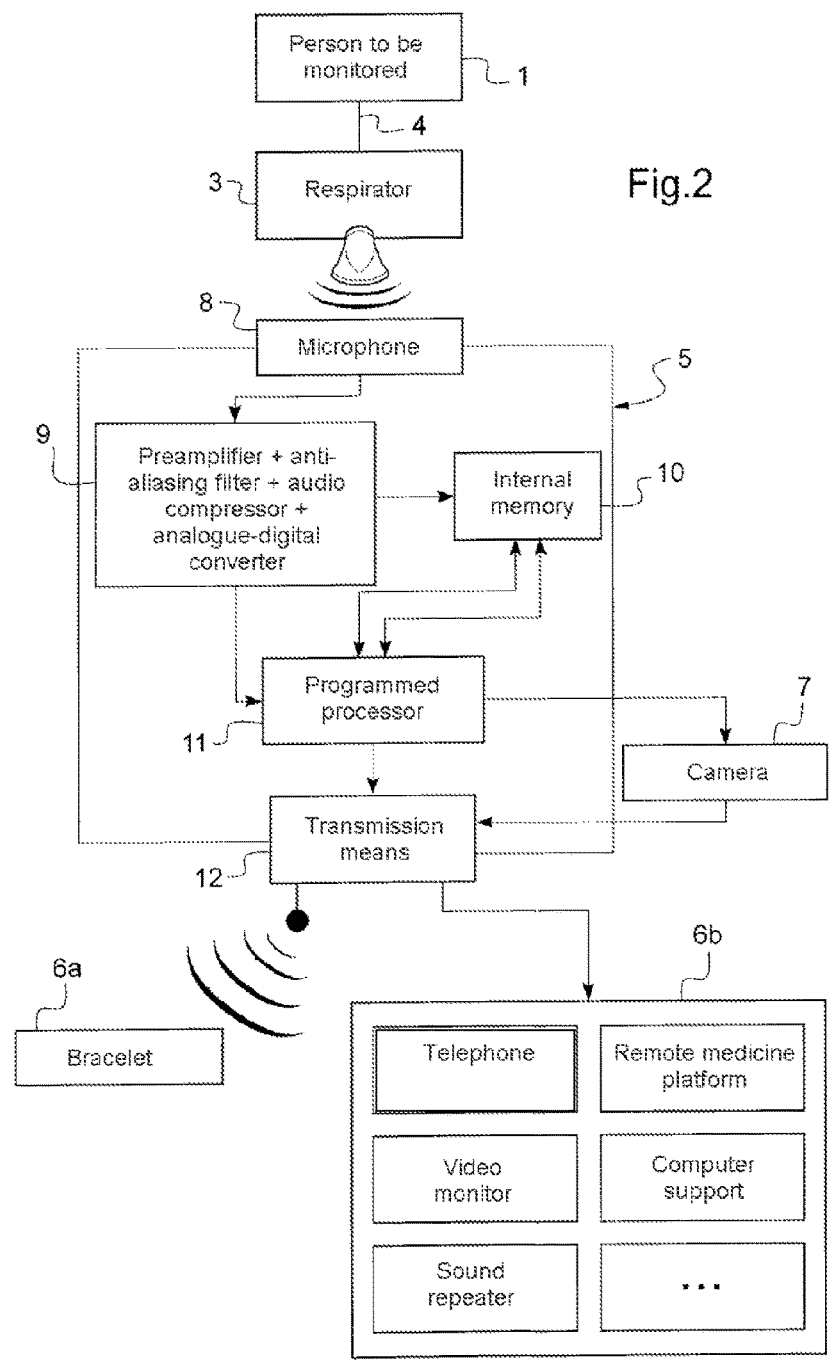

\# ASSISTANCE TERMINAL FOR REMOTELY MONITORING A PERSON CONNECTED TO A MEDICAL ASSISTANCE AND MONITORING DEVICE

Assistance terminal for remotely monitoring a person connected to a medical assistance and monitoring device.

The present invention relates to an assistance terminal that makes it possible to invoke the intervention of a person to be monitored and/or a remote monitor in the event of a worsening of the clinical state of the person to be monitored or of a malfunction of a medical assistance and monitoring device with which the assistance terminal is associated. The remote monitor may equally be a health professional or a non-professional aid.

BACKGROUND OF THE INVENTION

The document JP2006271821 discloses an assistance terminal connected to sensors indicating the state of operation of a respirator connected to a person to be monitored. In the event of a malfunction of the respirator, the respirator sends a signal that is immediately detected by the sensors and transmitted to the assistance terminal. The assistance terminal transmits the signal to a light device situated, for example, in a corridor and through a portable telephone and a remote medicine platform. The device also indicates the room and bed number, the name of the person to be monitored and the type of malfunction of the respirator.

However, this type of device provides only a relative level of safety for certain types of users. For example, people afflicted with Ondine's curse, characterized by a malfunction of the central nervous system, are liable, in a deep sleep phase, to suffer hypoventilation leading to an increase in the rate of carbon dioxide in the blood. Maintaining the primary vital functions of these people, such as regular and sufficient breathing, therefore entails using a respirator but also ongoing monitoring. For practical and economic reasons, the people to be monitored are looked after at home. In a non-medical environment, such as a home, the assistance terminal described by the document JP2006271821 does not allow for a rapid intervention on the person to be monitored or on the respirator. Should the respirator stop or suffer a malfunction, the person to be monitored cannot intervene on his or her own on the problem to be solved since he or she is often incapable of waking up and does not register that a signal is being sent to signal a malfunction.

Many devices of the same type, known from the prior art, comprise an assistance terminal included in the medical device. Thus, the assistance terminal cannot be adapted to already existing medical devices, such as a respirator.

The document WO 2009/153535 discloses an assistance terminal for remotely monitoring a person connected to a medical assistance and/or monitoring device that can be adapted to medical devices that already exist in hospitals. However, such a terminal simply transmits an alarm signal to a remote device situated, for example, in a corridor and via a portable telephone and a remote medicine platform, indicating only the room number from where the signal originates. Such a terminal cannot therefore be used everywhere because the presence of a third party is essential to intervene on the device when the latter emits a signal.

OBJECT OF THE INVENTION

The aim of the invention is therefore to propose an assistance terminal that can be adapted to any type of existing medical device capable of sending at least one signal, which at least partly obviates the abovementioned problems.

SUMMARY OF THE INVENTION

To this end, the subject of the invention is an assistance terminal for remotely monitoring a person connected to a medical assistance and/or monitoring device, the assistance terminal comprising a housing and at least one remote terminal, the housing comprising:
  reception means for receiving a signal from the medical device;
  conditioning means for conditioning the signal received by the reception means of the housing;
  storage means for, in a learning phase prior to a phase of use of the terminal, storing a range of signals which are sent by the medical device, and which are received by the reception means of the housing and which are conditioned by the conditioning means;
  comparison means for, during the phase of use of the terminal, comparing a signal sent by the medical device, received by the reception means and conditioned by the conditioning means, with the signals previously stored;
  transmission means for, during the phase of use, transmitting the signal, if the latter corresponds to a signal previously stored, to the remote terminal;
  the terminal comprising means for playing back the signal to at least one person to notify him or her of the sending of said signal by the device.

According to the invention, the signal playback means comprise means for sending at least one nociceptive stimulus to the person connected to the medical assistance and/or monitoring device.

The various reception, conditioning, storage, comparison and transmission means contribute to making the assistance terminal capable of adapting to any type of medical device. Depending on whether the signal sent by the medical device is audio, video, visual, electrical, etc., the reception means of the housing comprise receivers ensuring the reception of a range of signals sent by the medical device.

Advantageously, by conducting a novel learning phase, the assistance terminal can easily be reprogrammed in the event of a change of the associated medical device.

Moreover, the person notified of the sending of said signal is the person connected to the medical assistance and/or monitoring device so that the person to be monitored can intervene by himself or herself on his or her own clinical state or on the defective medical device. The assistance terminal according to the invention can thus be used equally for monitoring at home and in a hospital, the person connected to the medical device being independent.

BRIEF DESCRIPTION OF THE DRAWINGS

The invention will be better understood in light of the following description of a particular embodiment of the invention, in conjunction with the appended figures in which:
FIG. 2 is a functional diagram of the terminal of FIG. 1.

DETAILED DESCRIPTION OF THE INVENTION

Figure 1:
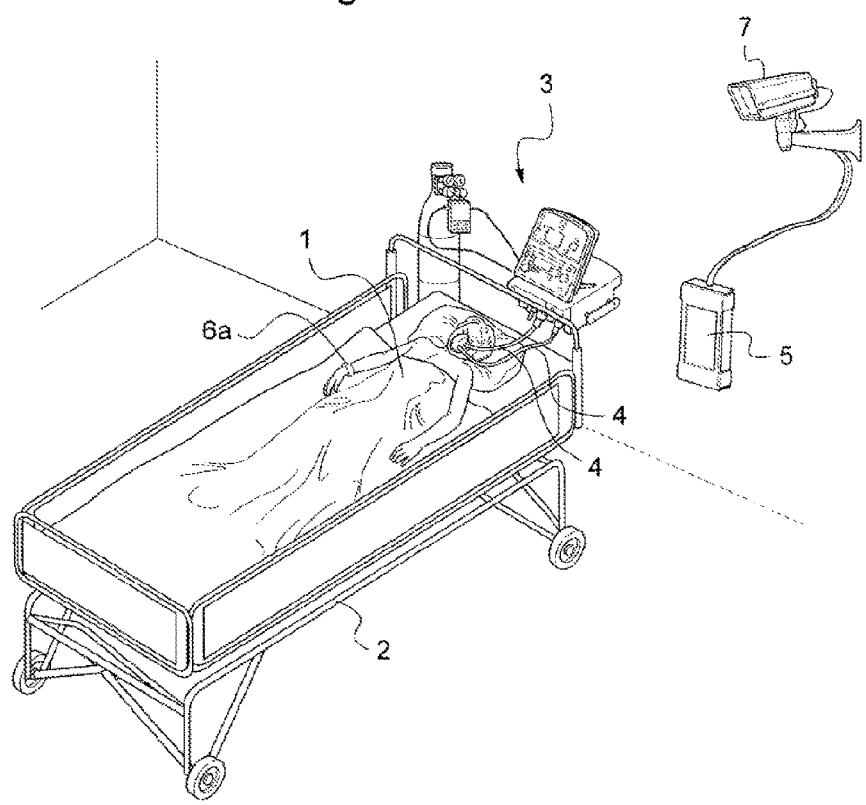
FIG. 1 is a view of a person to be monitored and of an assistance terminal according to the invention.

FIG. 1 represents a person to be monitored 1, located, for example, in his or her home, lying down in a bed 2. The person to be monitored 1 is connected to a medical assistance and/or monitoring device, for example here a respirator 3, which can ensure the breathing functions of the person to be monitored 1 by delivering artificial ventilation. The room in which the person to be monitored 1 is located also comprises a housing 5 positioned close to the respirator 3, capable of picking up signals, converting them, storing them, comparing them and transmitting them as explained later. The room also comprises at least one terminal. Here, the terminal comprises a bracelet 6a, fixed for example to the wrist of the person to be monitored 1. The housing 5 and the terminal 6a form an assistance terminal according to the invention. Other terminals may be arranged in or outside the home.

In the present embodiment, a camera 7 is connected to the housing 5 and transmits audio and video data via the housing 5.

In addition to the artificial ventilation function, the respirator 3 also provides ongoing monitoring of its own effectiveness by checking, on the one hand, the gas volume delivered to the person to be monitored 1 by comparing it to a volume prescribed by predefined settings, and by checking, on the other hand, the pressure which prevails in the pipes 4 linking the respirator 3 and the person to be monitored 1. When the volume delivered to the person to be monitored 1 is insufficient, or when the pressure in the pipes 4 is too high or too low (leak, blockage, disconnection, breathing stopped, etc.), the respirator 3 sends an alert signal, for example a sound signal.

FIG. 2 more particularly represents the operation of the assistance terminal of the invention.

In the embodiment presented, the housing 5 comprises:
reception means, such as a microphone 8, for receiving the audio signal or signals sent by the respirator 3;
conditioning means 9 for conditioning the signal or signals received;
storage means, such as an internal memory 10, for storing the signals conditioned during a learning phase;
means for comparing a received signal with the stored signals, here a processor 11 programmed by means of software performing the comparison of the signals; and
transmission means 12 for transmitting the signals if the latter are recognized by the comparison means as being sent by the respirator.

Generally, the sound signal or signals sent by the respirator 3 have frequencies of between 400 Hz and 4 KHz. One of the advantages of the assistance terminal is to be able to adapt to different types of medical devices. Consequently, in order to avoid being at the limits of detection of the signal or signals sent by the respirator 3, the microphone 8 is capable of picking up signals of between 200 Hz and 10 KHz for a sound pressure level greater than 40 dBA.

Before the use of the assistance terminal, the housing 5 must be parameterized so that the audio signal or signals sent by the respirator 3 can be recognized by the housing 5. The learning phase, prior to a phase of use of the terminal, consists in storing the range of signals sent by the respirator 3. For this, each of the audio signals sent by the respirator 3 are picked up by the microphone 8 to then be conditioned by the conditioning means 9 and finally stored in the internal memory 10 of the housing 5.

In the case of a change of the medical assistance and/or monitoring device associated with the assistance terminal, it is thus sufficient to reinitialize the learning phase to once again parameterize the housing 5.

In the embodiment described, the conditioning means 9 comprise a preamplifier, acting as a bandpass, an anti-aliasing filter, ensuring that none of the signals received has a frequency greater than 10 KHz, an audio compressor and an analogue-digital converter for the signals to be able to be stored in the internal memory 10 of the housing 5.

Once the learning phase has been completed, the assistance terminal can operate. Thus, in the event of a triggering of an audio signal sent by the respirator 3, the microphone 8 picks up the signal which is then conditioned, then compared with the signals previously stored using the processor 11. If the conditioned signal corresponds to one of the signals previously stored, the transmission means 12 transmit the signal to the bracelet 6a.

Here, the bracelet 6a, in contact with the person to be monitored 1, receives the signal transmitted by wireless transmission. The bracelet 6a comprises means for playing back the signal to the person to be monitored 1 to notify him or her of the sending of the signal by the medical device 3. According to the invention, the signal playback means comprise means for sending at least one nociceptive stimulus to the person to be monitored 1.

Here, the means for sending a nociceptive stimulus comprise a nociceptive device mounted on the bracelet 6a.

According to a preferred embodiment, the nociceptive device comprises means for generating electrical pulses to the person to be monitored 1. In the case of Ondine's curse, the electrical pulses are normally sufficient to wake up the person to be monitored even if the latter is in a deep sleep phase. The person is thus independent.

Preferably, the signal playback means are arranged to control the nociceptive device so that said nociceptive device progressively increases the electrical pulses transmitted, preferably until the nociceptive device is deactivated. Preferably, the electrical pulses are interrupted only if the signal sent by the respirator 3 is deactivated.

Preferentially, the signal playback means also comprise a vibratory device which is also mounted on the bracelet 6a.

In this way, it is thus possible to first send vibrations to the person to be monitored 1 before sending electrical pulses to him or her if the vibrations are not sufficient to make him or her react.

According to a particular embodiment, the signal playback means are arranged to control the vibratory and nociceptive devices so that vibrations are sent using the vibratory device and then electrical pulses are sent using the nociceptive device, instead of the vibrations, notably if the vibratory device is not deactivated by the end of a determined time interval from the sending of a first vibration. Preferably, the vibrations are interrupted only if the signal sent by the respirator 3 is deactivated.

Thus, if the person to be monitored 1 is woken up, the vibrations are sufficient to notify him or her that the medical device 3 is sending a signal. If the person to be monitored 1 is asleep and the vibrations are not sufficient to wake him or her up, the electrical pulses should normally wake up the person to be monitored even if the latter is in a deep sleep phase.

According to a preferred embodiment, the terminal 5 comprises a second terminal 6b comprising a video monitor to notifying a third person of the sending of the signal by the medical device. The video monitor receives at least video data from the camera 7 in the case of sending of the signal by the medical device 3.

Thus, in the case of triggering of an audio signal from the respirator 3, the person to be monitored 1 is able to be woken up and to intervene on his or her physical state or on the respirator. By virtue of the second terminal 6b, the third person is also notified of the anomaly.

Advantageously, in the case of sending of the signal by the medical device 3, the third person can first view the person to be monitored 1 via the video monitor and confirm whether he or she has to intervene or not. For example, if the person to be monitored wakes up by himself or herself and acts on the medical device to be monitored, the third person can easily check that his or her intervention is not necessary.

According to a preferred embodiment, the transmission means 12 are arranged to transmit the signal to the first terminal 6a then to the second terminal 6b instead of or in addition to the transmission of the signal to the first terminal. Preferentially, the transmission means 12 are arranged so that:
- vibrations are sent using the vibratory device;
- then that electrical pulses are sent using the nociceptive device, instead of or in addition to the vibrations, if the vibratory device is not deactivated by the end of a determined time interval from the sending of a first vibration;
- and finally that video data are sent to the video monitor of the second terminal 6b if the nociceptive device is not deactivated by the end of a determined time interval from the sending of the first electrical pulse.

According to a particular aspect of the invention and for safety reasons, the signal played back by the terminals 6a, 6b can be deactivated only in response to a detection by the respirator 3 of a return to normal of the respirator 3 according to the predefined parameters of the respirator 3. Preferentially, the signal played back is interrupted only if the signal sent by the respirator 3 is deactivated, which is the sign that someone has dealt with the problem signaled by the sending of the signal. Preferentially, the signal playback means of the first terminal (6a) and of the second terminal (6b) are arranged to deactivate the signal played back in response only:
- to a detection by the medical device 3 of an improvement in the clinical state of the person to be monitored 1 and the sending by the medical device 3 of a corresponding signal, or
- to the repair of a malfunction of the medical device 3 and the sending by the medical device 3 of a corresponding signal.

Obviously, the invention is not limited to the embodiment described above and is open to variants which will be apparent to a person skilled in the art without departing from the context of the invention as defined by the claims.

Obviously, the assistance terminal can be used with any medical assistance and/or monitoring device, and not only a respirator.

The assistance terminal according to the invention will also be able to fulfill functions other than those of monitoring a patient and of notifying the patient and/or a third person in the event of a problem. For example, the assistance terminal will be able to include means for storing the signals that it receives from the medical device. These signals will thus be able to be recovered for subsequent analysis. For example, in the case of Ondine's curse, the signals stored during the night will be able to be analyzed in the day.

Although in the example illustrated, the signal sent by the medical device is of sound type and consequently, the reception means 8 of the housing 5 is a microphone, the medical device will be able to send other types of signals, such as, for example, visual, electrical or other, and the reception means 8 of the housing 5 will be adapted to receive such signals.

The transmission means 12 will be able to be of any type. Preferentially, the transmission means 12 will depend on the placement of the associated terminal. If the terminal is close to or in contact with the person to be monitored, a wireless transmission mode, for example of Bluetooth type, will preferably be used. If the terminal is far away from the person to be monitored, the Internet network will, for example, be used. A telephone network will also be able to be used.

Moreover, the terminal 5 will be able to communicate with terminals other than a video monitor than those described, such as a telephone, a sound repeater, a remote medicine platform, any type of information processing support, such as a computer. Preferentially, the medical state of the patient will make it possible to determine with how many and which terminals the terminal 5 will be able to communicate. For example, for a patient with slight breathing difficulties, the terminal 5 will be able to be only in communication with the bracelet 6a. For a person having motor problems and severe breathing difficulties, it would be preferable for the terminal 5 to also be in communication with a second terminal, for example directly connected to an emergency service such as the French ambulance and emergency service SAMU.

Although here, it has been stated that the bracelet 6a comprises a vibratory device and a nociceptive device, the bracelet 6a will be able to comprise only the nociceptive device.

Similarly, the bracelet 6a will be able to comprise any signal playback means other than those described in combination with the means for sending a nociceptive stimulus. For example, the bracelet 6a will be able to also comprise a sound device which sends a sound alarm until the signal sent by the medical device 3 is deactivated in conjunction with the sending of nociceptive stimulus by the nociceptive device.

Thus, the bracelet 6a will be able to play back the signal by each device that it comprises in succession or simultaneously. For example, the bracelet 6a will be adapted initially to play back the signal by one of the devices that it comprises then, if the signal sent by the medical device is not deactivated, to play back the signal by another of the devices. The bracelet 6a will also be able to be adapted to play back the signal by the two devices at the same time if the signal sent by the medical device is not deactivated.

According to a particular embodiment, the signal playback means are arranged to control the vibratory and nociceptive devices so that vibrations are sent using the vibratory device and then electrical pulses are sent using the nociceptive device, in addition to the vibrations, if the vibratory device is not deactivated by the end of a determined time interval from the sending of a first vibration.

The invention claimed is:

1. An assistance terminal for remotely monitoring a person connected to a medical device that is a medical assistance and/or monitoring device, the assistance terminal comprising a housing and at least one remote terminal, the housing comprising:
reception means for receiving a signal from the medical device;
conditioning means for conditioning the signal received by the reception means of the housing;
storage means for, in a learning phase prior to a phase of use of the assistance terminal, storing a range of signals which are sent by the medical device, and which are received by the reception means of the housing and which are conditioned by the conditioning means;
comparison means for, during the phase of use of the assistance terminal, comparing a signal sent by the medical device, received by the reception means and conditioned by the conditioning means, with the signals previously stored;

transmission means for, during the phase of use, transmitting the signal to the at least one remote terminal, if the signal sent by the medical device corresponds to one of the signals previously stored;

the at least one remote terminal comprising signal playback means for playing back the signal to the person connected to the medical device or to another person to notify him or her of the sending of said signal by the medical device;

wherein the signal playback means comprise a nociceptive device for sending at least one nociceptive stimulus to the person connected to the medical device; and wherein the signal playback means are arranged to control the nociceptive device so that said nociceptive device progressively increases an intensity of the nociceptive stimulus so as to progressively increase the degree of the nociceptive stimulus in order to be able to wake up the person connected to the medical assistance and/or monitoring device even if the person is in a deep sleep phase.

2. The assistance terminal as claimed in claim 1, in which the at least one remote terminal comprises a bracelet intended to be worn by the person connected to the medical assistance and/or monitoring device, and wherein the nociceptive device is mounted on the bracelet.

3. The assistance terminal as claimed in claim 2, in which the nociceptive device comprises means for generating electrical pulses to the person connected to the medical assistance and/or monitoring device.

4. The assistance terminal as claimed in claim 2, in which the signal playback means also comprise a vibratory device which is mounted on the bracelet.

5. The assistance terminal as claimed in claim 4, in which the signal playback means are arranged to control the nociceptive and vibratory devices so that vibrations are sent using the vibratory device and then electrical pulses are sent using the nociceptive device, instead of or in addition to the vibrations.

6. The assistance terminal as claimed in claim 1, in which the reception means comprise a camera, the transmission means being capable of transmitting a video signal generated by the camera.

7. The assistance terminal as claimed in claim 6, comprising a second terminal which comprises a video monitor receiving the video signal.

8. The assistance terminal as claimed in claim 7, in which the transmission means are arranged to transmit the signal to the at least one remote terminal then to the second terminal instead of or in addition to the transmission of the signal to the at least one remote terminal.

9. The assistance terminal as claimed in claim 1, in which the signal playback means of the remote terminal are arranged to deactivate the signal played back in response only:

to a detection by the medical device of an improvement in the clinical state of the person connected to the medical assistance and/or monitoring device and the sending by the medical device of a corresponding signal, or to the repair of a malfunction of the medical device and the sending by the medical device of a corresponding signal.

10. An assistance terminal for remotely monitoring a person connected to a medical assistance and/or monitoring device, the assistance terminal comprising a housing and a remote terminal, the housing comprising:

a receiver that receives a signal from the medical device;

a conditioning circuit that conditions the signal received by the receiver;

memory storing a range of signals that are sent by the medical device in a learning phase prior to a phase of use of the terminal;

a processor that, during the phase of use of the terminal, compares a signal sent by the medical device, received by the receiver and conditioned by the conditioning circuit, with the range of signals previously stored in the memory;

a transmitter that, if the signal corresponds to an abnormal value requiring attention, transmits the signal to the remote terminal; and the remote terminal is configured to send a nociceptive stimulus to the person connected to the medical assistance and/or monitoring device and to progressively increase an intensity of the nociceptive stimulus so as to progressively increase the degree of the nociceptive stimulus in order to be able to wake up the person connected to the medical assistance and/or monitoring device even if the person is in a deep sleep phase.

11. The assistance terminal according to as claimed in claim 10, wherein the receiver is a microphone.

12. The assistance terminal according to as claimed in claim 10, wherein the conditioning circuit comprises a preamplifier, an anti-aliasing filter, and an analogue-digital converter.

13. A method for monitoring a sleeping person connected to a medical assistance and/or monitoring device using the assistance terminal according to claim 10, comprising:

receiving a signal at the receiver from the medical device;

conditioning the signal received by the receiver with the condition circuit;

storing in memory a range of signals that are sent by the medical device in a learning phase prior to a phase of use of the terminal;

during the phase of use of the terminal, comparing signals sent by the medical device with the range of signals previously stored in the memory;

transmitting with the transmitter the signal to the remote terminal, if the signal corresponds to an abnormal value requiring intervention;

sending via the remote terminal a nociceptive stimulus to the sleeping person and progressively increasing an intensity of the nociceptive stimulus, nor more than a maximum value, until the sleeping person wakes up and intervenes.

14. The method according to claim 13, wherein the sleeping person is afflicted with Ondine's curse.

15. The method according to claim 13, wherein the signals sent by the medical device are representative of the sleeping person's breathing function.

16. The method according to claim 13, wherein the sleeping person is connected to a respirator and the signals sent by the medical device are representative of the sleeping person's current respiratory condition.

17. An assistance terminal for remotely monitoring a person connected to a medical device that is a medical assistance and/or monitoring device, the assistance terminal comprising a housing and at least one remote terminal, the housing comprising:

reception means for receiving a signal from the medical device;

conditioning means for conditioning the signal received by the reception means of the housing;

storage means for, in a learning phase prior to a phase of use of the assistance terminal, storing a range of signals which are sent by the medical device, and which are received by the reception means of the housing and which are conditioned by the conditioning means;

comparison means for, during the phase of use of the assistance terminal, comparing a signal sent by the medical device, received by the reception means and conditioned by the conditioning means, with the signals previously stored;

transmission means for, during the phase of use, transmitting the signal to the at least one remote terminal, if the signal sent by the medical device corresponds to one of the signals previously stored;

the at least one remote terminal comprising signal playback means for playing back the signal to the person connected to the medical device or to another person to notify him or her of the sending of the signal by the medical device; the signal playback means comprises a nociceptive device for sending at least one nociceptive stimulus to the person connected to the medical device, the nociceptive stimulus being different from vibration or thermal stimulus, wherein the signal playback means are arranged to control the nociceptive device so that said nociceptive device, progressively increases an intensity of the nociceptive stimulus.

18. An assistance terminal for remotely monitoring a person connected to a medical device that is a medical assistance and/or monitoring device, the assistance terminal comprising a housing and at least one remote terminal, the housing comprising:

reception means for receiving a signal from the medical device;

conditioning means for conditioning the signal received by the reception means of the housing;

storage means for, in a learning phase prior to a phase of use of the assistance terminal, storing a range of signals which are sent by the medical device, and which are received by the reception means of the housing and which are conditioned by the conditioning means;

comparison means for, during the phase of use of the assistance terminal, comparing a signal sent by the medical device, received by the reception means and conditioned by the conditioning means, with the signals previously stored;

transmission means for, during the phase of use, transmitting the signal to the at least one remote terminal, if the signal sent by the medical device corresponds to one of the signals previously stored;

the at least one remote terminal comprising signal payback means for playing back the signal to the person connected to the medical device or to another person to notify him or her of the sending of said signal by the medical device; the signal playback means comprise a nociceptive device for sending at least one nociceptive stimulus to the person connected to the medical device, wherein the signal playback means are arranged to control the nociceptive device so that said nociceptive device progressively increases an intensity of the nociceptive stimulus in order to be able to wake up the person connected to the medical assistance and/or monitoring device even if the person is in a deep sleep phase.

19. The assistance terminal as claimed in claim 1, wherein the at least one nociceptive stimulus is in the form of electrical pulses.

20. An assistance terminal for remotely monitoring a person connected to a medical device that is a medical assistance and/or monitoring device, the assistance terminal comprising a housing and at least one remote terminal, the housing comprising:

reception means for receiving a signal from the medical device;

conditioning means for conditioning the signal received by the reception means of the housing;

storage means for, in a learning phase prior to a phase of use of the assistance terminal, storing a range of signals which are sent by the medical device, and which are received by the reception means of the housing and which are conditioned by the conditioning means;

comparison means for, during the phase of use of the assistance terminal, comparing a signal sent by the medical device, received by the reception means and conditioned by the conditioning means, with the signals previously stored;

transmission means for, during the phase of use, transmitting the signal to the at least one remote terminal, if the signal sent by the medical device corresponds to one of the signals previously stored;

the at least one remote terminal comprising signal playback means for playing back the signal to the person connected to the medical device or to another person to notify him or her of the sending of said signal by the medical device;

wherein the signal playback means comprise a nociceptive device for sending at least one nociceptive stimulus to the person connected to the medical device; and wherein the signal playback means are arranged to control the nociceptive device so that said nociceptive device progressively increases an intensity of the nociceptive stimulus, wherein the signal playback means of the remote terminal are arranged to deactivate the signal played back in response only:
to a detection by the medical device of an improvement in the clinical state of the person connected to the medical assistance and/or monitoring device and the sending by the medical device of a corresponding signal, or
to the repair of a malfunction of the medical device and the sending by the medical device of a corresponding signal.

* * * * *